United States Patent
Lu et al.

(10) Patent No.: US 7,245,692 B2
(45) Date of Patent: Jul. 17, 2007

(54) X-RAY IMAGING SYSTEMS AND METHODS USING TEMPORAL DIGITAL SIGNAL PROCESSING FOR REDUCING NOISE AND FOR OBTAINING MULTIPLE IMAGES SIMULTANEOUSLY

(75) Inventors: Jianping Lu, Chapel Hill, NC (US); Otto Z. Zhou, Chapel Hill, NC (US); Jian Zhang, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 11/410,997

(22) Filed: Apr. 25, 2006

(65) Prior Publication Data

US 2007/0053489 A1  Mar. 8, 2007

Related U.S. Application Data

(60) Provisional application No. 60/674,537, filed on Apr. 25, 2005.

(51) Int. Cl.
*A61B 6/03* (2006.01)

(52) U.S. Cl. .................. 378/4; 378/9; 378/19; 378/122

(58) Field of Classification Search ........... 250/370.09; 378/4, 9, 16, 19, 21–26, 62, 98.8, 122
See application file for complete search history.

(56) References Cited

U.S. PATENT DOCUMENTS 3,932,756 A * 1/1976 Cowell et al. .......... 250/361 R
4,712,226 A 12/1987 Horbaschek
4,809,308 A 2/1989 Adams et al.
4,926,452 A 5/1990 Baker et al.
5,594,770 A 1/1997 Bowles et al.
5,692,028 A 11/1997 Geus et al.
5,764,683 A 6/1998 Swift et al.
5,773,921 A 6/1998 Keesmann et al.
6,028,911 A 2/2000 Kawahara
6,057,637 A 5/2000 Zettl et al.
6,097,138 A 8/2000 Nakamoto (Continued)

OTHER PUBLICATIONS

Dobbins III et al., "Digital x-ray tomosynthesis: current state of the art and clinical potential," Phys. Med. Biol. 48 (2003) R65-R106.

(Continued)

*Primary Examiner*—Edward J. Glick
*Assistant Examiner*—John M Corbett
(74) *Attorney, Agent, or Firm*—Jenkins, Wilson, Taylor & Hunt, P.A.

(57) ABSTRACT

X-ray imaging systems and methods are provided that use temporal digital signal processing for reducing noise and for obtaining multiple images simultaneously. An x-ray imaging system can include an x-ray source adapted to generate a pulsed x-ray beam having a predetermined frequency and apply the pulsed x-ray beam to an object to be imaged. An x-ray detector can be adapted to detect x-ray radiation from the object and generate temporal data based on the x-ray radiation. A temporal data analyzer can be adapted to apply a temporal signal process to the temporal data to remove at least a portion of the temporal data having a different frequency than the predetermined frequency.

54 Claims, 13 Drawing Sheets

U.S. PATENT DOCUMENTS

| | | | |
|---|---|---|---|
| 6,097,788 A * | 8/2000 | Berenstein et al. | 378/92 |
| 6,125,167 A | 9/2000 | Morgan | |
| 6,178,226 B1 * | 1/2001 | Hell et al. | 378/113 |
| 6,192,104 B1 | 2/2001 | Adams et al. | |
| 6,277,318 B1 | 8/2001 | Bower et al. | |
| 6,280,697 B1 | 8/2001 | Zhou et al. | |
| 6,333,968 B1 | 12/2001 | Whitlock et al. | |
| 6,334,939 B1 | 1/2002 | Zhou et al. | |
| 6,385,292 B1 | 5/2002 | Dunham et al. | |
| 6,456,691 B2 | 9/2002 | Takahashi et al. | |
| 6,498,349 B1 | 12/2002 | Thomas et al. | |
| 6,545,396 B1 | 4/2003 | Ohki et al. | |
| 6,553,096 B1 | 4/2003 | Zhou et al. | |
| RE38,223 E | 8/2003 | Keesmann et al. | |
| 6,621,887 B2 * | 9/2003 | Albagli et al. | 378/42 |
| 6,630,772 B1 | 10/2003 | Bower et al. | |
| 6,650,730 B2 | 11/2003 | Bogatu et al. | |
| 6,674,837 B1 * | 1/2004 | Taskar et al. | 378/122 |
| RE38,561 E | 8/2004 | Keesmann et al. | |
| 6,787,122 B2 | 8/2004 | Zhou | |
| 6,850,595 B2 | 2/2005 | Zhou et al. | |
| 6,852,973 B2 | 2/2005 | Suzuki et al. | |
| 6,876,724 B2 | 4/2005 | Zhou et al. | |
| 6,965,199 B2 | 11/2005 | Stoner et al. | |
| 6,980,627 B2 | 12/2005 | Qiu et al. | |
| 7,027,558 B2 * | 4/2006 | Ghelmansarai et al. | 378/65 |
| 7,046,757 B1 * | 5/2006 | Bani-Hashemi et al. | 378/7 |
| 7,085,351 B2 | 8/2006 | Lu et al. | |
| 7,147,894 B2 | 12/2006 | Zhou et al. | |
| 2002/0085674 A1 | 7/2002 | Price et al. | |
| 2002/0094064 A1 | 7/2002 | Zhou et al. | |
| 2002/0140336 A1 | 10/2002 | Stoner et al. | |
| 2003/0102222 A1 | 6/2003 | Zhou et al. | |
| 2003/0198318 A1 | 10/2003 | Price et al. | |
| 2004/0028183 A1 | 2/2004 | Lu et al. | |
| 2004/0036402 A1 | 2/2004 | Keesmann et al. | |
| 2004/0114721 A1 | 6/2004 | Qiu et al. | |
| 2004/0240616 A1 | 12/2004 | Qiu et al. | |
| 2004/0256975 A1 | 12/2004 | Gao et al. | |
| 2005/0226361 A1 | 10/2005 | Zhou et al. | |

OTHER PUBLICATIONS

Moore et al., "Three-Dimensional X-Ray Laminography as a Tool for Detection and Characterization of BGA Package Defects", IEEE Transactions on Components and Packaging Technologies, vol. 25, No. 2, Jun. 2002.

Yue et al., "Generation of continuous and pulsed diagnostic imaging x-ray radiation using a carbon-nanotube-based field-emission cathode," Applied Physics Letters, vol. 81, No. 2: pp. 355-357 (2002).

Sugie et al., "Carbon nanotubes as electron source in an x-ray tube," Applied Physics Letters, vol. 78, No. 17: pp. 2578-2580 (2001).

Cheng et al., Dynamic radiography using a carbon-nanotube-based field-emission x-ray source, Review of Scientific Instruments, vol. 75, No. 10: pp. 3264-3267.

Charbonnier et al., "Resolution of Field-Emission X-Ray Sources," Radiology, vol. 117: pp. 165-172 (1974).

Hallenbeck, "Clinical Evaluation of the 350-kV Chest Radiography System," Radiology, vol. 117: pp. 1-4 (1974).

Ribbing et al., "Diamond membrane based structures for miniature X-ray sources," Diamond and Related Materials, vol. 11: pp. 1-7 (2002).

Gao et al., "Fabrication and Electron Field Emission Properties of Carbon Nanotube Films by Electrophoretic Deposition," Advanced Materials, vol. 13, No. 23 (2001).

Resat et al., "Microbeam developments and applications: A low linear energy transfer perspective," Cancer and Metastasis Reviews 23: p. 323-331 (2004).

International Search Report for corresponding International Application No. PCT/US05/47066 dated Oct. 6, 2006.

* cited by examiner

X-RAY IMAGING SYSTEMS AND METHODS USING TEMPORAL DIGITAL SIGNAL PROCESSING FOR REDUCING NOISE AND FOR OBTAINING MULTIPLE IMAGES SIMULTANEOUSLY

CROSS-REFERENCE TO RELATED APPLICATION

This non-provisional patent application claims the benefit of U.S. Provisional Application No. 60/674,537, filed Apr. 25, 2005, the disclosure of which is incorporated by reference herein in its entirety.

GOVERNMENT INTEREST

This invention was made with U.S. Government support under grant number N00014-98-1-0597 awarded by the Office of Naval Research. The U.S. Government has certain rights in the invention.

TECHNICAL FIELD

The subject matter disclosed herein relates to x-ray imaging. More particularly, the subject matter disclosed herein relates to x-ray imaging systems and methods using temporal digital signal processing for reducing noise and for enhancing imaging acquisition speed by obtaining multiple images simultaneously.

BACKGROUND ART

X-ray imaging is widely used in many areas including medial diagnostics and treatment, industrial inspection and testing, security screening and detections. In current x-ray imaging systems, an x-ray beam is generated and applied to a three-dimensional (3-D) object for projecting the object onto a two-dimensional (2-D) panel detector. The projection may be reconstructed into 2-D and 3-D images. Typically, noise is produced along the direction of the x-ray beam and results in reduced resolution of the object image. Noise can originate from the object to be imaged, an x-ray detector detecting the x-ray radiation, electronic circuits, and various other sources.

One exemplary x-ray imaging system is a computed tomography (CT) system. CT enables reconstruction of a 3-D image of an object by acquiring hundreds to thousands of 2-D projection images from different projection angles. In many current CT scanners, a single x-ray tube is mechanically rotated around an object for collecting multiple projection images required for reconstructing an image of the object. The process of mechanically rotating the x-ray tube limits the rate of data acquisition. Further, the control of such systems is complicated by the process of mechanically rotating the x-ray tube. Many current CT scanners acquire 2-D projection images from one viewing angle at a time. Thus, the speed of the CT scanner is limited.

X-ray systems that have improved object imaging speed include ultra-fast electron beam CT scanner systems and printed circuit board (PCB) inspection systems. In these systems, an electromagnetic field steers an electron beam to different positions on an x-ray target to produce a scanning x-ray beam. Such systems can be large, costly, and include a limited range of viewing angles. X-ray imaging systems that are smaller, less costly, and include a greater range of viewing angles are desirable.

Another desirable improvement for x-ray imaging systems is increased resolution of object images. Resolution can be improved by reducing noise contained in the x-ray data used for image generation. Noise reduction in x-ray data can also result in a reduction in the strength of x-ray radiation required for object imaging. A reduction in the strength of x-ray radiation can be beneficial for mammography and imaging of microelectronics, applications requiring minimized x-ray dosages.

Accordingly, in light of desired improvements associated with x-ray imaging systems, there exists a need for improved x-ray imaging system functionality and related methods.

SUMMARY

In accordance with this disclosure, novel x-ray imaging systems and methods using temporal digital signal processing for reducing noise and for obtaining multiple images simultaneously are provided.

It is an object of the present disclosure therefore to provide novel x-ray imaging systems and methods using temporal digital signal processing for reducing noise and for obtaining multiple images simultaneously. This and other objects as may become apparent from the present disclosure are achieved, at least in whole or in part, by the subject matter described herein.

BRIEF DESCRIPTION OF THE DRAWINGS

Preferred embodiments of the subject matter described herein will now be described with reference to the accompanying drawings, of which.

DETAILED DESCRIPTION

Figure 1:
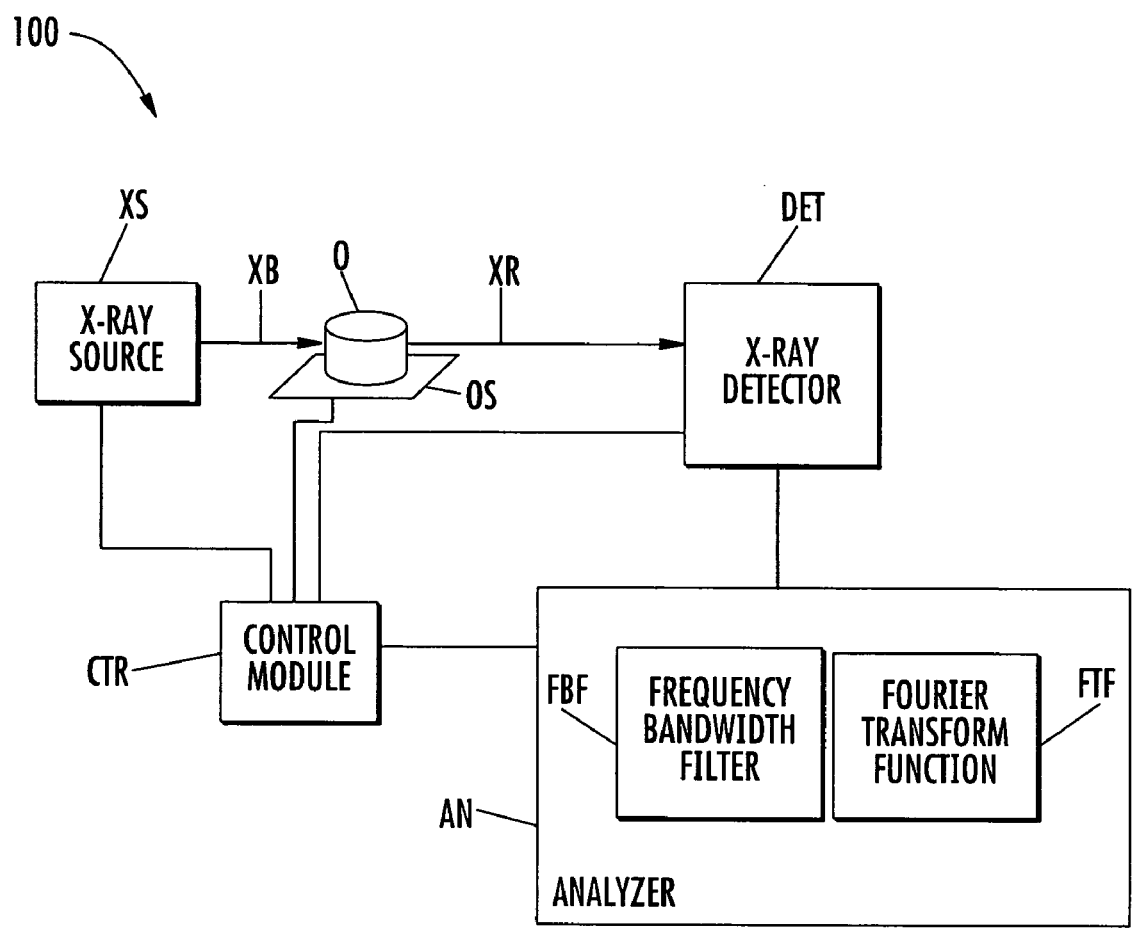
FIG. 1 is a block diagram of a single-beam x-ray imaging system according to an embodiment of the subject matter described herein.

In accordance with the present disclosure, x-ray imaging systems and methods using temporal digital signal processing for reducing noise and for obtaining multiple images simultaneously are provided. The systems and methods described herein can have particular application for use in radiographic imaging, including CT, tomosynthesis, fluoroscopy, angiography, multi-energy radiography, and x-ray fluorescence spectroscopy analysis. Other exemplary applications include medical diagnostics and treatment, industrial non-destructive testing (NDT) and x-ray fluorescence (XRF) analysis, and security screening and detection. An x-ray imaging system according to the present disclosure can include an x-ray source adapted to generate a pulsed x-ray beam having a predetermined frequency and to apply the pulsed x-ray beam to an object to be imaged. Further, an x-ray imaging system according to the present disclosure can include an x-ray detector adapted to detect x-ray radiation from the object and generate temporal data based on the x-ray radiation. An x-ray imaging system according to the present disclosure can also include a temporal data analyzer adapted to apply a temporal digital signal process to the temporal data to remove at least a portion of the temporal data having a different frequency than the predetermined frequency. The removed portion of the temporal data having the different frequency can correspond to noise in the detected x-ray radiation. As a result, signal-to-noise ratio of the x-ray data is improved for enhancing images of the object generated using the temporal data. Further, an x-ray imaging system according to the present disclosure can reduce x-ray flux needed in imaging techniques such as digital radiography and fluorescence spectroscopy.

Further, an x-ray imaging system according to the subject matter described herein can include a multi-pixel x-ray source operable to be programmable for generating multi-beam x-ray radiation. The system can include a digital x-ray detector operable to record temporal x-ray radiation for each pixel. Further, the system can include a data processor operable to perform power spectrum analysis based on the recorded data and differentiate frequency components. The system can acquire multi-projection images simultaneously for enabling a multi-fold increase in imaging speed in CT scanner applications and other imaging applications.

The temporal signal processing techniques described herein provide the ability to reduce noise not associated with the x-ray source. These techniques can advantageously enhance the signal-to-noise ratio to make it possible for low dosage imaging. Further, these techniques can be used for applications such as breast CT and tomosynthesis, where maintaining low total dosage per projection image can be desired. The techniques described herein can also lead to new radiography applications such as ultra-low dosage pediatric radiography.

The term "x-ray source" is used herein to designate devices that can generate x-ray radiation in a programmable way. The waveform of the x-ray radiation can be periodic or aperiodic, and continuous or pulsed. Exemplary x-ray sources can produce x-rays using electron field emitters including nano-structured materials.

The term "temporal digital signal process" is used herein to designate any digital processing of temporal data, including Fourier analysis and wavelet analysis.

FIG. 1 is a block diagram of a single-beam x-ray imaging system according to an embodiment of the subject matter described herein. Referring to FIG. 1, an x-ray imaging system, generally designated 100, can include an x-ray source XS operable to generate a pulsed x-ray beam XB of a predetermined pulsing frequency and apply x-ray beam XB to an object O to be imaged. Object O can be positioned in the path of x-ray beam XB for intercepting at least a portion of x-ray beam XB. The intercepted portion of x-ray beam XB can be absorbed by object O and/or pass through object O. Another portion of x-ray beam XB can pass around object O.

X-ray source XS can be any suitable device operable to generate an x-ray beam for imaging an object. An exemplary x-ray source can be a field emission x-ray source. Exemplary field emission x-ray sources are described in U.S. Pat. No. 6,553,096 to Zhou et al., filed Oct. 6, 2000 and issued Apr. 22, 2003; U.S. Pat. No. 6,850,595 to Zhou et al., file Dec. 4, 2002 and issued Feb. 1, 2005; and U.S. Pat. No. 6,876,724 to Zhou et al., filed Jan. 22, 2002 and issued Apr. 5, 2005, the disclosures of which are incorporated by reference herein. A unique property of field emission x-ray sources is their ability to generate x-ray pulses in arbitrary temporal waveform.

In one example, system 100 can include an object stage OS for holding object O in position for intercepting x-ray beam XB. Object stage OS can be a controllable rotation stage for rotating object O in different directions such that different sides of object O are exposed to x-ray beam XB.

Further, system 100 can include an x-ray detector DET operable to detect x-ray radiation XR. Detector DET can continuously detect the x-ray intensity of x-ray radiation XR over a period of time. The detected x-ray radiation XR can include the portion of x-ray beam XB passing through object O and/or past object O. X-ray radiation XR can also include noise generated by imaging objects, detector DET, electronic circuits, or various other sources. Further, x-ray detector DET can generate temporal x-ray data based on x-ray radiation XR. The temporal x-ray data can be generated by recording the x-ray intensity of x-ray radiation as a function of time with a sampling interval less than the pulse width of x-ray beam XB for a desired dwell time. The temporal x-ray data can be represented as an electrical signal and stored.

X-ray detector DET can be any suitable device operable to detect x-ray radiation. In one example, x-ray detector DET can be a high-frame-rate digital detector. In another example, x-ray detector DET can be one or more Si-PIN photodiode x-ray detectors. Examples of digital x-ray detectors include, but are not limited to, charge-coupled device (CCD) area detectors, amorphous selenium (a-Se) area detectors, amorphous silicon (a-Si) area detectors, and arrays of Si-PIN photodiode x-ray detectors.

Further, system 100 can include a temporal data analyzer AN operable to apply a temporal digital signal process to the temporal x-ray data to remove at least a portion of the temporal x-ray data having a different frequency than the predetermined pulsing frequency of x-ray beam XB. Most of the noise detected by x-ray detector DET does not have a unique temporal power spectrum with a unique frequency or correlation with x-ray source XS. Noise can be reduced or removed by discarding temporal x-ray data having a different pulsing frequency than x-ray beam XB. By removing the portion of the temporal x-ray data having a different frequency than the predetermined pulsing frequency, the signal-to-noise ratio of the x-ray data is improved for enhancing images of object O generated using the temporal x-ray data.

In one example, after a predetermined number of x-ray pulses are generated by x-ray detector DET, a temporal series of the detected data can be processed by a temporal Fourier transform function FTF to produce a frequency domain power spectrum. A single frequency bandwidth filter FBF can filter and discard components of the power spectrum that do not correspond to the pulsing frequency of x-ray beam XB. The portion of the temporal x-ray data having a different frequency than the predetermined frequency can correspond to noise in the detected x-ray radiation XR. The portion of the temporal x-ray data having a frequency that is the same as the predetermined frequency can be used for imaging object O.

According to one embodiment, temporal Fourier analysis can be applied to the temporal x-ray data for removing the portion of the temporal x-ray data having a frequency that is different than the predetermined frequency.

According to another embodiment, a temporal encoding technique can be used for generating pulsed x-ray beam XB. For example, x-ray beam XB can be wavelet encoded. Temporal wavelet decoding can be applied to the temporal x-ray data for removing the portion of the temporal x-ray data having components different than the predetermined encoding scheme.

System 100 can also include a control module CTR operable to execute instructions for controlling x-ray source XS, x-ray detector DET, and analyzer AN for imaging object O. The executable instructions can be implemented as a computer program product embodied in a computer readable medium. Exemplary computer readable media can include disk memory devices, chip memory devices, application specific integrated circuits, programmable logic devices, downloadable electrical signals, and/or any other suitable computer readable media. Further, control module CTR can include hardware, software, and/or firmware, such as memory (e.g., RAM, ROM, and computer-readable disks), transistors, capacitors, resistors, inductors, logic circuitry, and other components suitable for individually controlling x-ray source XS, x-ray detector DET, and analyzer AN for imaging object O. Control module CTR may also control object stage OS for rotating object O. Further, control module CTR can control the frequency and pulse width of x-ray radiation XR.

Figure 2:
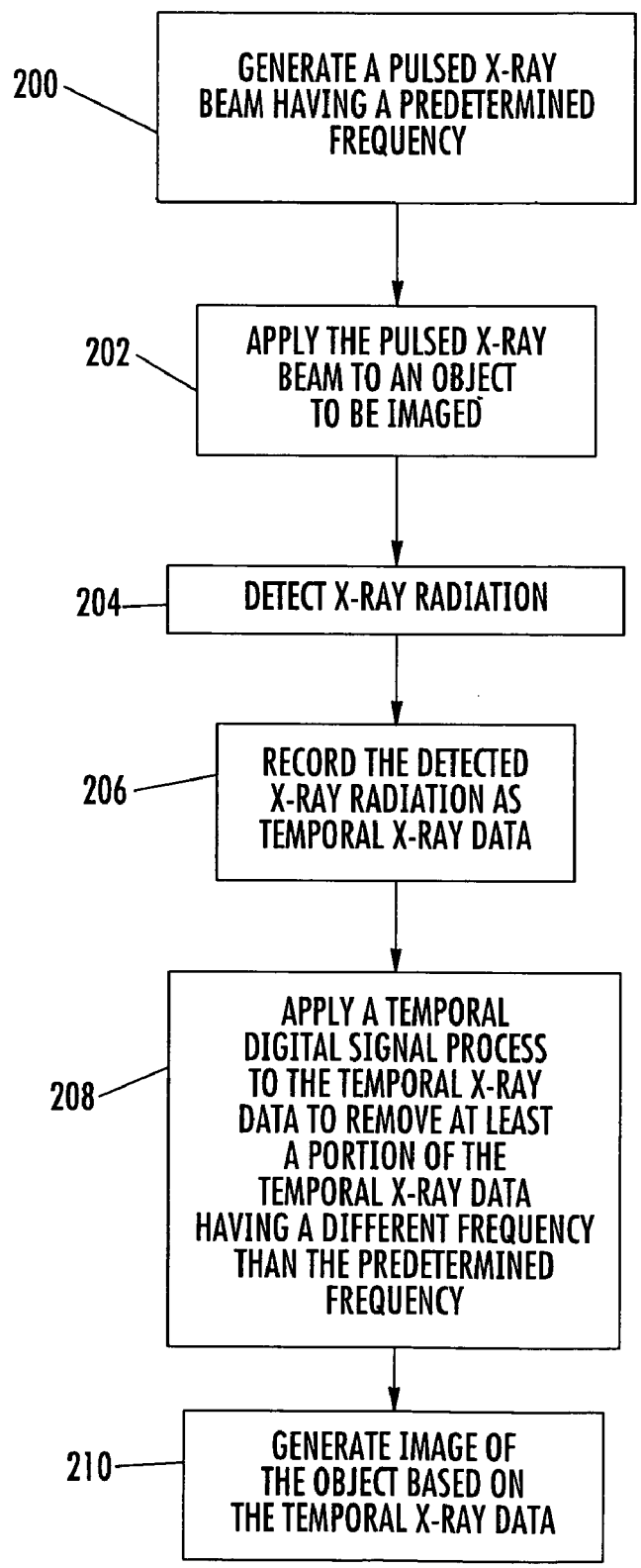
FIG. 2 is a flow chart illustrating an exemplary process for imaging an object using a single beam x-ray imaging system according to an embodiment of the subject matter described herein.

FIG. 2 is a flow chart illustrating an exemplary process for imaging an object using a single-beam x-ray imaging system (such as system 100 shown in FIG. 1) according to an embodiment of the subject matter described herein. Referring to FIG. 2, block 200 includes generating a pulsed x-ray beam having a predetermined frequency. In block 202, the generated x-ray beam can be applied to an object to be imaged. For example, x-ray source XS of FIG. 1 can generate pulsed x-ray beam XB having a predetermined frequency and apply x-ray beam XB to object O. Exemplary frequencies include, but are not limited to, about 1 Hz to about 1 MHz. Exemplary x-ray beam intensities include, but are not limited to, about 0.001 mA to about 10,000 mA. Exemplary x-ray energies includes, but are not limited to, about 10 keV to about 1,000 keV.

In block 204, x-ray radiation can be detected. The x-ray radiation can include a portion of x-ray beam XB passing through object O and/or past object O. The detected x-ray radiation can also include noise. For example, x-ray detector DET can detect x-ray radiation XR including x-ray beam XB passing through or past object O and noise.

In block 206, the detected x-ray radiation can be recorded as temporal x-ray data. A temporal digital signal process can be applied to the temporal x-ray data for removing at least a portion of the temporal x-ray data having a different frequency than the predetermined pulsing frequency of x-ray beam XB (block 208). Next, in block 210, an image of object O can be generated based on the temporal x-ray data. The temporal digital process (DSP) can include Fourier analysis and power spectrum analysis. DSP filters the signals detected by detector DET that are not generated by x-ray source XS. The process can be carried out for one or more pixels, either in sequence or in parallel. The processing can be performed by software and/or or hardware. The hardware may include one or more digital signal processors operable to simultaneously receive multiple projection images of object O. The collection of projection images from different angles can be used to reconstruct 3-D images of the object through CT reconstruction algorithms and/or tomosynthesis algorithms.

Figure 3:
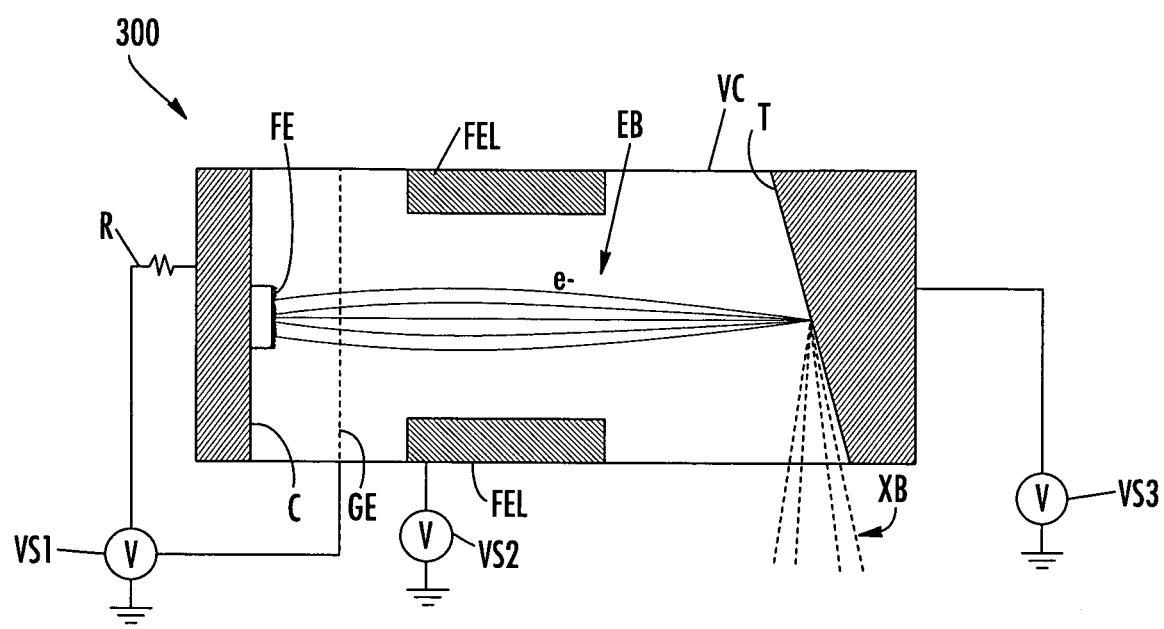
FIG. 3 is a schematic, cross-sectional side view of a field emission x-ray source according to an embodiment of the subject matter described herein.

FIG. 3 is a schematic, cross-sectional side view of a field emission x-ray source, generally designated 300, according to an embodiment of the subject matter described herein. Referring to FIG. 3, x-ray source 300 can include an electron field emitter FE (also referred to herein as a "pixel") for emitting electrons. Electron field emitter FE can comprise one or more carbon nanotubes and/or other suitable electron field emission materials. Exemplary electron field emission materials can include nanotubes, nanorods, Spindt tips, and nanoparticles of diamond. Carbon nanotubes are typically nano-structured or nanostructure material such as nanoparticles with particle sizes less than 100 nm. Electron field emitter FE can be coupled to a surface of a cathode C, conductive or contact line, or other suitable conductive material for receiving current.

Electron field emitter FE can be controlled by a controller (such as control module CTR shown in FIG. 1) to emit electrons for producing an electron beam EB. In one embodiment, a controller can control a voltage source VS1 to apply a voltage between electron field emitter FE and a gate electrode GE to generate an electric field for extracting electrons from electron field emitter FE. The applied voltage can be pulsed for generating a pulsed electron beam EB. Thus, the frequency of x-ray beam XB can be controlled by the frequency of the applied extraction electric field.

Electron field emitter FE can be oriented such that extracted electrons are directed towards an anode target structure T. Target structure T can produce an x-ray beam XB of a desired wavelength upon bombardment by pulsed electron beam EB. X-ray source 300 can include a focusing electrode FEL for focusing electrons extracted from electron field emitters FE on target structure T and thus reducing the size of electron beam EB. Focusing electrode FEL can be controlled by application of voltage to focusing electrode FEL by voltage source VS2. A voltage source VS3 can apply a voltage between gate electrode GE and target structure T for accelerating electrons emitted by field emitters FE towards target structure T.

A vacuum chamber VC can include a sealed interior for containing electron field emitter FE and gate electrode GE. The interior of vacuum chamber VC can be evacuated to achieve a desired interior pressure. An exemplary interior pressure of vacuum chamber VC can be about $10^{-7}$ Torr. Electron beam EB can travel from the interior of vacuum chamber VC to its exterior through an electron permeable portion or window.

Figure 4A:
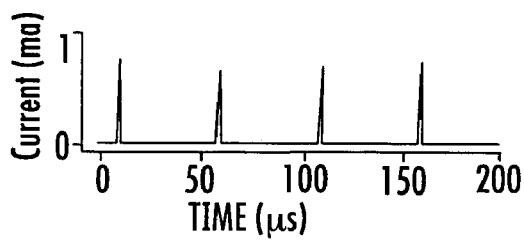
FIGS. 4A–4C are graphs illustrating different current that can be applied to a field emitter shown in FIG. 3 over a period of time for generating a pulsed x-ray beam.
Figure 4B:
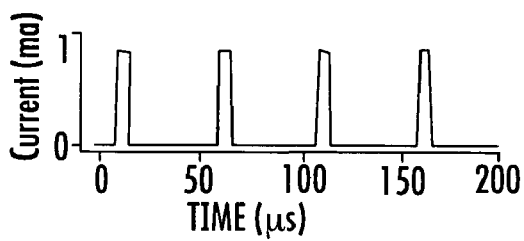
Figure 4C:
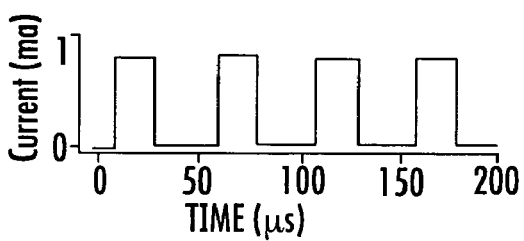

FIGS. 4A-4C illustrate graphs of different current that can be applied to field emitter FE (shown in FIG. 3) over a period of time for generating a pulsed x-ray beam XB (shown in FIG. 3). FIG. 4A shows the application of about a 1 milliamp (mA) pulse of current having a width of about 0.5 microseconds (μs) at a constant repetition rate of about 20 kilohertz (kHz). FIG. 4B shows the application of about a 1 milliamp (mA) pulse of current having a width of about 8 microseconds (μs) at a constant repetition rate of about 20 kilohertz (kHz). FIG. 4C shows the application of about a 1 milliamp (mA) pulse of current having a width of about 45 microseconds (μs) at a constant repetition rate of about 20 kilohertz (kHz).

Figure 5A:
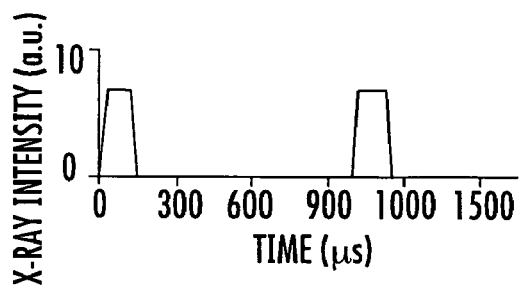
FIGS. 5A–5C are graphs illustrating x-ray intensities of x-ray beams of different pulsing frequencies generated by an x-ray source.
Figure 5B:
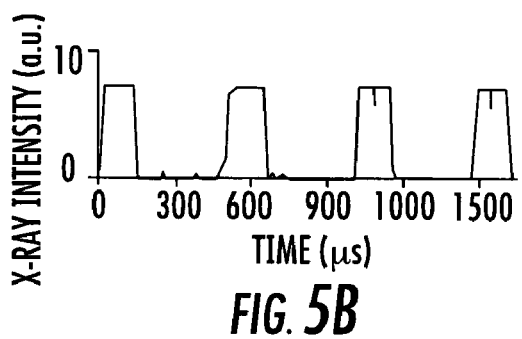
Figure 5C:
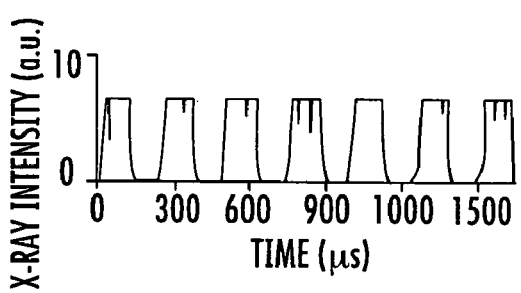

FIGS. 5A-5C illustrate graphs of x-ray intensities of x-ray beams of different pulsing frequencies generated by an x-ray source such as x-ray source shown in FIG. 1. The x-ray beams have a constant width of about 150 μs. FIG. 5A shows an x-ray intensity of a pulsed x-ray beam having a frequency of about 950 hertz. FIG. 5B shows an x-ray intensity of a pulsed x-ray beam having a frequency of about 1900 hertz. FIG. 5C shows an x-ray intensity of a pulsed x-ray beam having a frequency of about 3800 hertz.

A multi-pixel x-ray imaging system according to the subject matter described herein can generate multi-projection images of an object. A multi-pixel x-ray imaging system can include an x-ray source operable to pulse a plurality of x-ray beams of different frequencies at an object to be imaged. The pulsed x-ray beams can be applied to different sides of the object. X-ray radiation resulting from the irradiation of the object can be detected by one or more x-ray detectors. When two or more of the x-ray beams are radiating with unique frequencies, the detected temporal series of x-ray data is a superposition of radiations from the radiating beams. By processing the temporal x-ray data through a temporal digital signal process, the frequency domain power spectrum for each pixel (or the whole image of the object) can be decomposed into distinct components from the multiple x-ray beams. Each component can correspond to a unique x-ray beam generated from a specific pixel. As a result, multiple projection images can be simultaneously obtained using a single x-ray detector. One advantage of applying multiple images to CT imaging, or any other suitable imaging modality that require multi-projection images, is the substantially increase in image data acquisition speed. These imaging modality can include CT, tomosynthesis, fluoroscopy, angiography, and dynamic radiography.

Similar imaging techniques can be applied when different beams in the multi-pixel, x-ray imaging system have different x-ray energy spectra. Different x-ray energy spectra can be achieved by using different anode KVp or different anode materials. In this way, the imaging system can enable fast imaging in dual energy imaging and multi-energy imaging.

Figure 6:
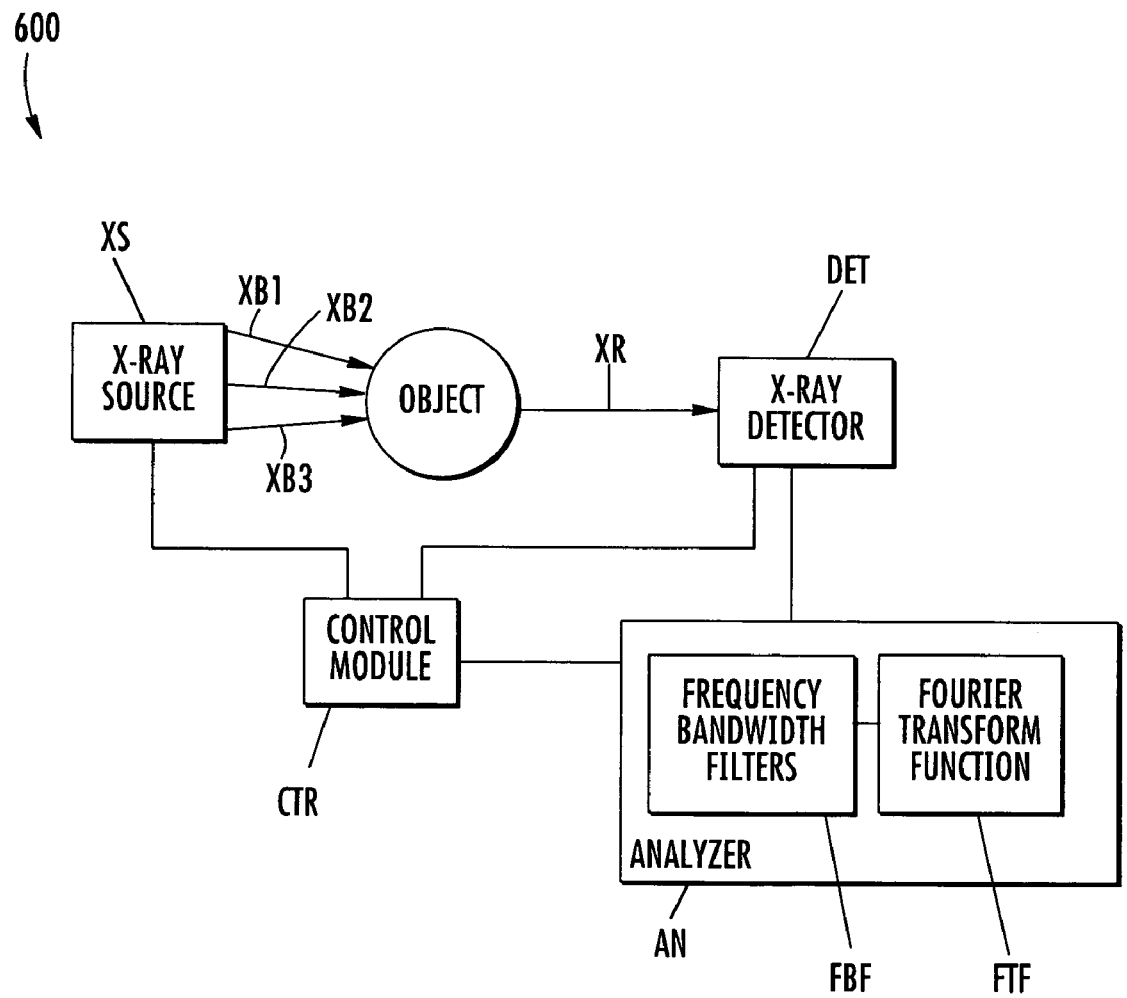
FIG. 6 is a block diagram of a multi-pixel, x-ray imaging system for simultaneously acquiring of multi-view projection images according to an embodiment of the subject matter described herein.

FIG. 6 is a block diagram of a multi-pixel, x-ray imaging system for simultaneously acquiring of multi-view projection images according to one embodiment of the subject matter described herein. Referring to FIG. 6, a multi-pixel, x-ray imaging system, generally designated 600, can include an x-ray source XS operable to generate a plurality of pulsed x-ray beams XB1-XB3 and apply the pulsed x-ray beams to an object O to be imaged. The pulsed x-ray beams can be applied to object O from several different angles, or from multi-projection angles. Each x-ray beam XB1-XB3 can be pulsed at a different temporal frequency. For example, x-ray beams XB1-XB3 can be pulsed at predetermined frequencies $\omega 1$, $\omega 2$, and $\omega 3$, respectively.

X-ray source XS can be any suitable device operable to generate multiple x-ray beams having different temporal frequencies. An exemplary x-ray source can be a multi-pixel, field emission x-ray source. Exemplary field emission x-ray sources are described in U.S. Pat. Nos. 6,533,096 and 6,850,595, the disclosures of which are incorporated by reference herein.

System 600 can include an x-ray detector DET operable to detect x-ray radiation XR, which can be the portions of x-ray beams XB1-XB3 passing through object O and noise. Detector DET can be an ultra-fast, high frame rate x-ray detector operable to detect and store x-ray radiation pulsed at frequencies $\omega 1$, $\omega 2$, and $\omega 3$. Further, x-ray detector DET can generate temporal x-ray data based on x-ray radiation XR. The temporal x-ray data can be generated by recording the x-ray intensity of x-ray radiation as a function of time with a sampling interval less than the pulse width of x-ray beam XB for a desired dwell time. The temporal x-ray data can be represented as an electrical signal and stored.

Further, system 600 can include a temporal data analyzer AN operable to apply a temporal signal process to the temporal x-ray data to resolve x-ray data having the same frequencies as the predetermined frequencies of x-ray beams XB1-XB3. Analyzer AN can also remove at least a portion of the temporal x-ray data having different frequencies than the predetermined frequencies. In particular, after a predetermined number of x-ray pulses are generated by x-ray detector DET, a temporal series of the detected data can be processed by a temporal Fourier transform function FTF to produce frequency domain power spectrum. Frequency bandwidth filters FBF can filter and discard the components that do not correspond to the pulsing frequencies of x-ray beams XB1-XB3. The portion of the temporal x-ray data having different frequencies than the predetermined frequencies of x-ray beams XB1-XB3 can correspond to noise in the detected x-ray radiation XR. The portion of the temporal x-ray data having frequencies that are the same as the predetermined frequencies $\omega 1$, $\omega 2$, and $\omega 3$ can be used for imaging object O. By removing the portion of the temporal x-ray data having different frequencies than the predetermined frequencies, the signal-to-noise ratio of the x-ray data is improved for enhancing images of object O generated using the temporal x-ray data. After temporal Fourier analysis, the x-ray data is decomposed into distinct frequency components corresponding to frequencies $\omega 1$, $\omega 2$, and $\omega 3$. The frequency components can be used for forming projection images of object O by corresponding x-ray beams. Thus, multi-projection images can be simultaneously obtained in the same time period as single projection imaging. Further, the frequency components can be correlated to form a 3-D image of object O.

System 600 can also include a control module CTR operable to execute instructions for controlling x-ray source XS, x-ray detector DET, and analyzer AN for imaging object O.

By utilizing a multi-pixel, x-ray imaging system, such as system 600, multi-projection images of an object from multi-x-ray sources can be simultaneously obtained using a single detector. Further, these techniques can enhance the imaging speed in CT, tomosynthesis, fluoroscopy, angiography, and multi-energy radiography. These techniques can also provide enhanced detection speed in industrial applications such as NDT and XRF.

Figure 7:
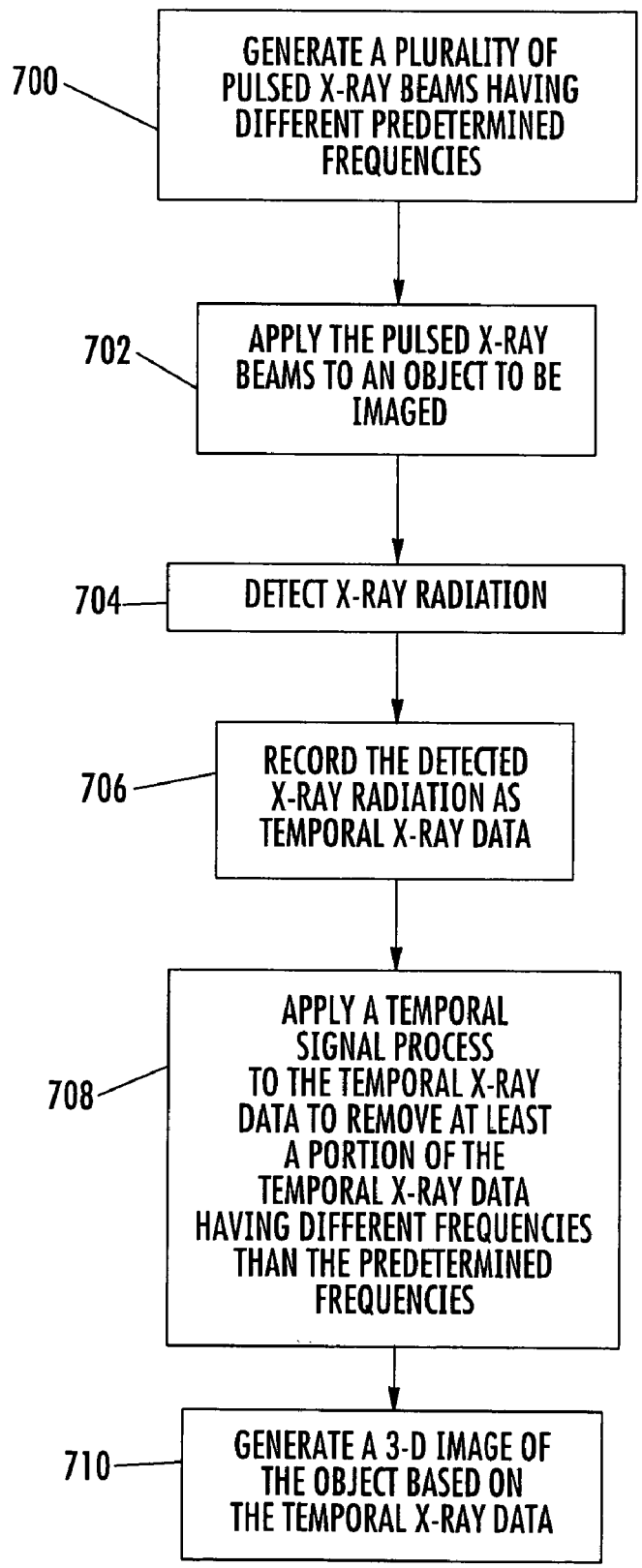
FIG. 7 is a flow chart illustrating an exemplary process for imaging an object using a multi-pixel, x-ray imaging system according to an embodiment of the subject matter described herein.

FIG. 7 is a flow chart illustrating an exemplary process for simultaneously acquiring of multi-view projection images (such as system 600 shown in FIG. 6) according to an embodiment of the subject matter described herein. Referring to FIG. 7, block 700 includes generating a plurality of pulsed x-ray beams having different predetermined frequencies ($\omega_k$). In block 702, the pulsed x-ray beams can be applied simultaneously or at different times to an objected to be imaged. For example, x-ray source XS of FIG. 6 can generate a plurality of pulsed x-ray beams XB1-XB3 having different predetermined frequencies and apply the pulsed x-ray beams to object O. The x-ray beams can advance to object O at different projection angles.

According to another embodiment, a temporal encoding technique can be used for generating pulsed x-ray beams XB1-XB3. For example, x-ray source can be wavelet encoded x-ray beams XB1-XB3. Analyzer AN can apply temporal wavelet decoding to the temporal x-ray data for extracting the x-ray radiation from different wavelet components.

In block 704, x-ray radiation can be detected. The x-ray radiation can include a portion of x-ray beams XB1-XB3 passing through object O and/or past object O. Further, the detected x-ray radiation can include noise. For example, x-ray detector DET shown in FIG. 6 can detect x-ray radiation XR including x-ray beams XB1-XB3 passing through or past object O and noise. X-ray detector DET can output temporal data d(x, y, t) for each pixel (x, y) that generates a beam. The pixels can be identified by coordinates x and y.

In block 706, the detected x-ray radiation can be recorded as temporal x-ray data. A temporal digital signal process can be applied to the temporal x-ray data to extract the x-ray signals with the predetermined pulsing frequencies (block 708). For example, the temporal data d(x, y, t) can be processed through a temporal Fourier transform for obtaining frequency domain spectrum d(x, y, $\omega$). The kth principle component corresponds to the x-ray beam generated from the x-ray source operating at $\omega_k$ frequency. The number of distinct frequencies can be two, ten, hundreds, or thousands. Next, in block 710, at least a portion of the temporal x-ray data having the different frequencies than the predetermined frequencies can be removed. In block 712, images of object O can be generated. For example, the kth principle component can be used to form the projection image from the kth x-ray beam. By this exemplary method, projection images can be obtained simultaneously during an exposure time of a single projection image and using a single detector.

Figure 8:
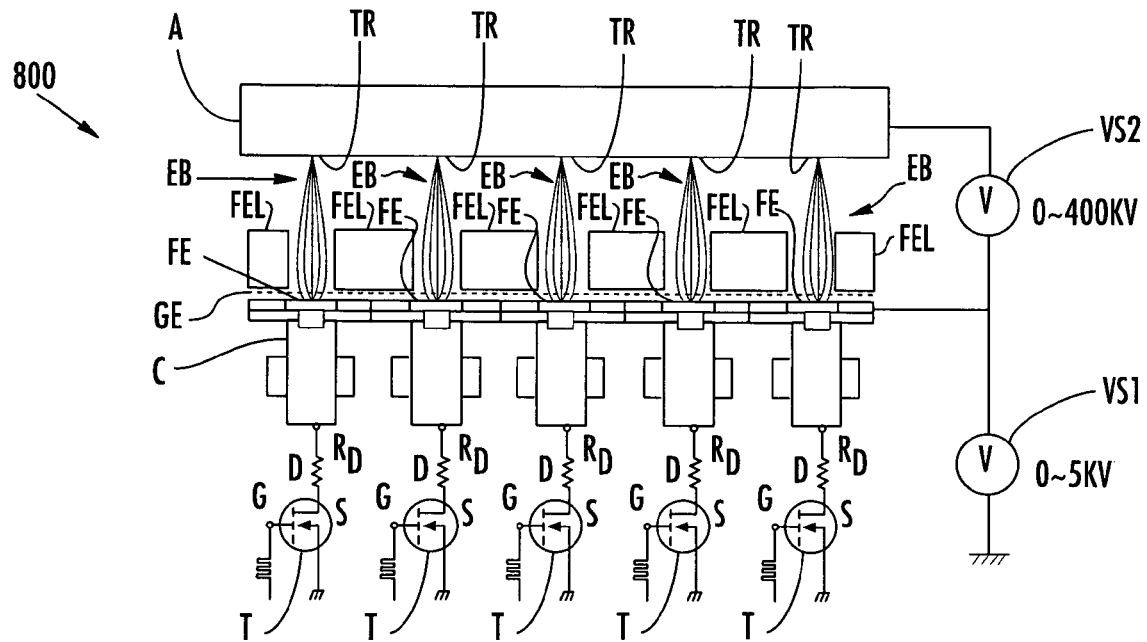
FIG. 8 is a schematic, cross-sectional side view of a multi-pixel, field emission x-ray source according to an embodiment of the subject matter described herein.

FIG. 8 is a schematic, cross-sectional side view of a multi-pixel field emission x-ray source, generally designated 800, according to an embodiment of the subject matter described herein. Referring to FIG. 8, x-ray source 800 can include a plurality of electron field emitters FE for emitting electrons. Electron field emitters FE can comprise one or more carbon nanotubes and/or other suitable electron field emission materials. Further, electron field emitters FE can be attached to a surface of respective cathodes C, conductive or contact line, or other suitable conductive material. Electron field emitters can be carbon nanotubes. The pixels can be evenly spaced with a center-to-center spacing of about 1.27 cm. Electron field emitters FE can be a 1.5 mm diameter carbon nanotube film coated on a metal disc. Each pixel can be operable to emit a current of 1 mA.

Electron field emitters FE can be controlled by a controller (such as control module CTR shown in FIG. 6) to emit electrons for producing respective electron beams EB. In one embodiment, a controller can control voltage sources VS1 to apply voltages between electron field emitters FE and gate electrodes GE to generate respective electric fields for extracting electrons from electron field emitters FE. The applied voltages can be pulsed at different frequencies for generating pulsed electron beams EB of different frequencies. In particular, the controller can individually operate a plurality of metal-oxide-semiconductor field-effect transistors (MOSFETs) T for individually controlling field emitters FE to emit electrons. The controller can individually control the voltage applied to field emitters FE for individually turning transistors on and off. The drains of transistors T can be connected to a corresponding one of a plurality of cathodes C. Each cathode C can be connected to a respective field emitter FE via a resistor such as a 100 kilo ohm protection resistor R. Transistors T can be turned on and off by the individual application of a high signal (e.g., 5 V) and a low signal (e.g., 0 V), respectively, to the gates of transistors T. When a high signal is applied to the gate of a transistor, a drain-to-source channel of the transistor is turned on to apply a voltage difference between a respective cathode C and gate electrode GE. A voltage difference exceeding a threshold can generate an electric field between cathode C and gate electrode GE such that electrons are extracted from respective electron field emitters FE. Conversely, when a low voltage (e.g., 0 V) is applied to the gate of a transistor, a corresponding drain-to-source channel is turned off such that the voltage at electron field emitter FE is electrically floating and the voltage difference between a respective cathode C and gate electrode GE cannot generate an electric field of sufficient strength to extract electrons from the respective electron field emitter. The controller is operable to individually apply voltage pulses of different frequencies to the gates of transistors T. Thus, the controller can individually control the frequencies of the electron beam pulses from field emitters FE.

Further, x-ray source 800 can include an anode A. A voltage difference can be applied between anode A and gate electrode GE such that respective fields are generated for accelerating electrons emitted by respective electron field emitters FE towards respective target structures TR. Target structures TR can be made of molybdenum. Target structures TR can produce x-ray beams having a desired pulse frequency upon bombardment by electron beams EB. X-ray source 800 can include a focusing electrode FEL for focusing electrons extracted from electron field emitters FE on target structure T and thus reduce the size of electron beam EB. Focusing electrode FEL can be controlled by application of voltage to focusing electrode FEL by voltage source VS2. In one embodiment, the anode voltage can be about 400 kV. The gate voltage can be varied depending on required flux.

A vacuum chamber VC can include a sealed interior for containing electron field emitters FE and gate electrode GE. The interior of vacuum chamber VC can be evacuated to achieve a desired interior pressure. An exemplary interior pressure of vacuum chamber VC can be about $10^{-7}$ Torr. Electron beam EB can travel from the interior of vacuum chamber VC to its exterior through an electron permeable portion or window. In one example, the electron permeable portion or window can be 4" diameter beryllium (Be) x-ray window.

Figure 9:
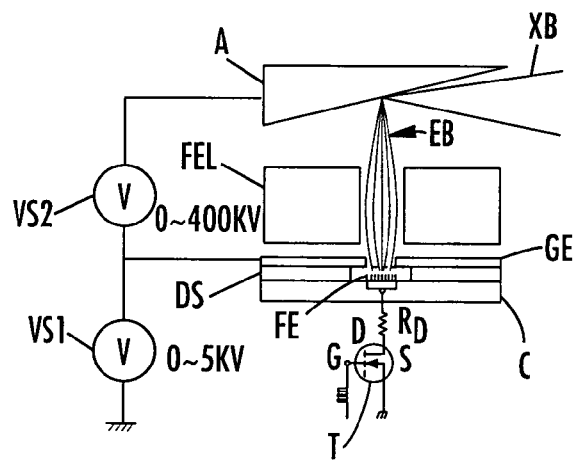
FIG. 9 is a schematic, cross-sectional side view of an x-ray unit of the x-ray source shown in FIG. 8 for generating a single, pulsed x-ray beam according to an embodiment of the subject matter described herein.

FIG. 9 is a schematic, cross-sectional side view of an x-ray unit 900 of x-ray source 800 shown in FIG. 8 for generating a single, pulsed x-ray beam XB according to an embodiment of the subject matter described herein. X-ray unit 900 represents a single pixel of x-ray source 800. Referring to FIG. 9, x-ray unit 900 can include an electron field emitter FE deposited on a cathode C. In one example, electron field emitter FE can be a 1.5 mm diameter carbon nanotube film. The carbon nanotube film can be deposited on a surface of a metal substrate. Further, the carbon nanotube film can be deposited on the surface by an electrophoretic process.

X-ray unit 900 can include a gate electrode GE for extracting electrodes on application of voltage by voltage source VS1. In one example, gate electrode GE can be a tungsten grid. Gate electrode GE can be spaced from cathode C by a dielectric spacer DS. In one example, dielectric spacer DS can be about 150 µm in thickness.

In one embodiment, x-ray beam XB can be generated by applying a constant DC voltage to anode A and a variable DC voltage (less than about 1 kV) to gate electrode GE. An n-channel MOSFET T can be adapted for switching on and off the emission of electrons from electron field emitter FE. A pixel can be activated by applying a 5 V signal to open the channel of MOSFET T such that electron field emitter FE forms a complete electrical circuit with gate electrode GE. Electron field emitter FE can be electrically coupled to a drain of MOSFET T. The source of MOSFET T can be grounded. The gate of MOSFET T can be connected to the output of a digital I/O board adapted to provided a 5 V DC voltage signal.

Electrons can be emitted from field emitter FE when the voltage applied by voltage source VS1 is greater than the critical field for emission. The emitted electrons can be accelerated by application of a voltage across anode A and gate electrode GE by voltage source VS2. The electrons form an electron beam EB that bombard an area of anode A to generate x-ray beam XB. A voltage can be applied to a focusing electrode FEL for focusing electron beam EB onto a target focal spot of anode A.

Referring again to FIG. 8, a scanning x-ray beam from different origins on a target of anode A can be produced by sweeping a pulsed controlling signal having a predetermined pulse width across each MOSFET in x-ray source 800. At each MOSFET that the signal is swept, a channel of the MOSFET can be opened for producing an x-ray beam from the corresponding focal point on the anode target.

A subset of the pixels can be activated such that the subset of pixels emits electrons with the same pulsing frequencies which generate x-ray beams from different focal points with the same frequencies. Alternatively, a pixel subset can be activated such that the subset of pixels emits electrons with different pulsing frequencies which generate x-ray beams from different focal points with different frequencies. In one embodiment, a subset of pixels can be activated by using separate gate electrons for the subset of pixels. Extraction voltages can be applied to the corresponding pixels with predetermined pulsing frequencies to generate field emitted electrons with the desired pulsing frequencies and amplitudes.

In another embodiment, a subset of pixels can be activated by using a common gate for all of the electron emitting pixels. The electron beam can be pulsed by pulsing the activation voltage applied to the MOSFET circuit. For example, in order to generate a pulsed x-ray beam with a predetermined frequency, a pulsed voltage with the predetermined frequency can be applied to open the corresponding MOSFET.

Figure 10A:
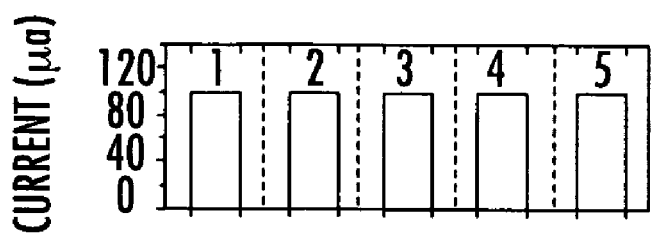
FIGS. 10A and 10B are graphs illustrating experimentally measured cathode current and voltage, respectively, from five pixels shown in FIG. 8.
Figure 10B:
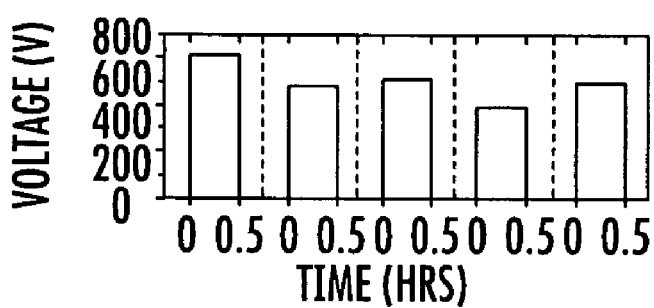

FIGS. 10A and 10B illustrate graphs of experimentally measured cathode current and voltage, respectively, from five pixels shown in FIG. 8. The current and voltage were measured over a 30 minute period under a constant current mode using a 100% duty cycle. The set cathode current was 100 µA. The anode voltage was set to 400 kV.

Figure 11:
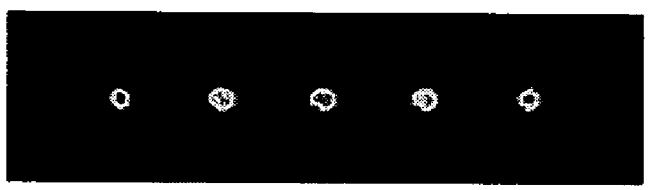
FIG. 11 is an image of pin-hole measurements of x-ray generating spots for the five pixels shown in FIG. 8.
Figure 12:
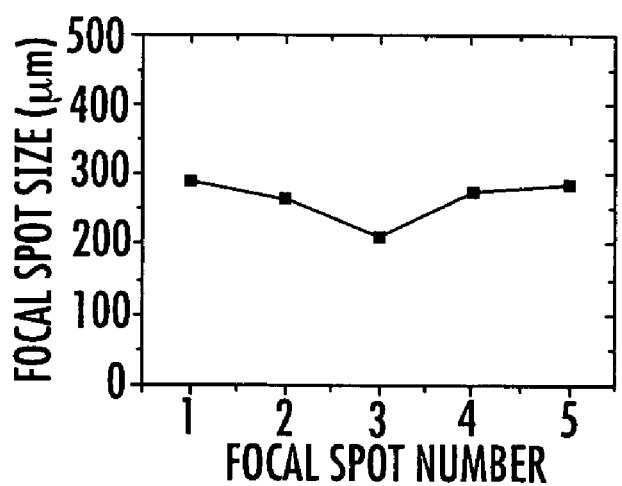
FIG. 12 is a graph illustrating sizes of the focal spots shown in FIG. 11.

FIG. 11 illustrate an image of pin-hole measurements of x-ray generating spots for the five pixels shown in FIG. 8. The pin-hole measurements show five evenly-spaced focal spots on a target. FIG. 12 illustrates a graph of sizes of the focal spots shown in FIG. 11. The sizes of the focal spots range between about 200 µm and 300 µm in diameter under a focusing voltage of about 900 V.

Figures 13A, 13B, 13C:
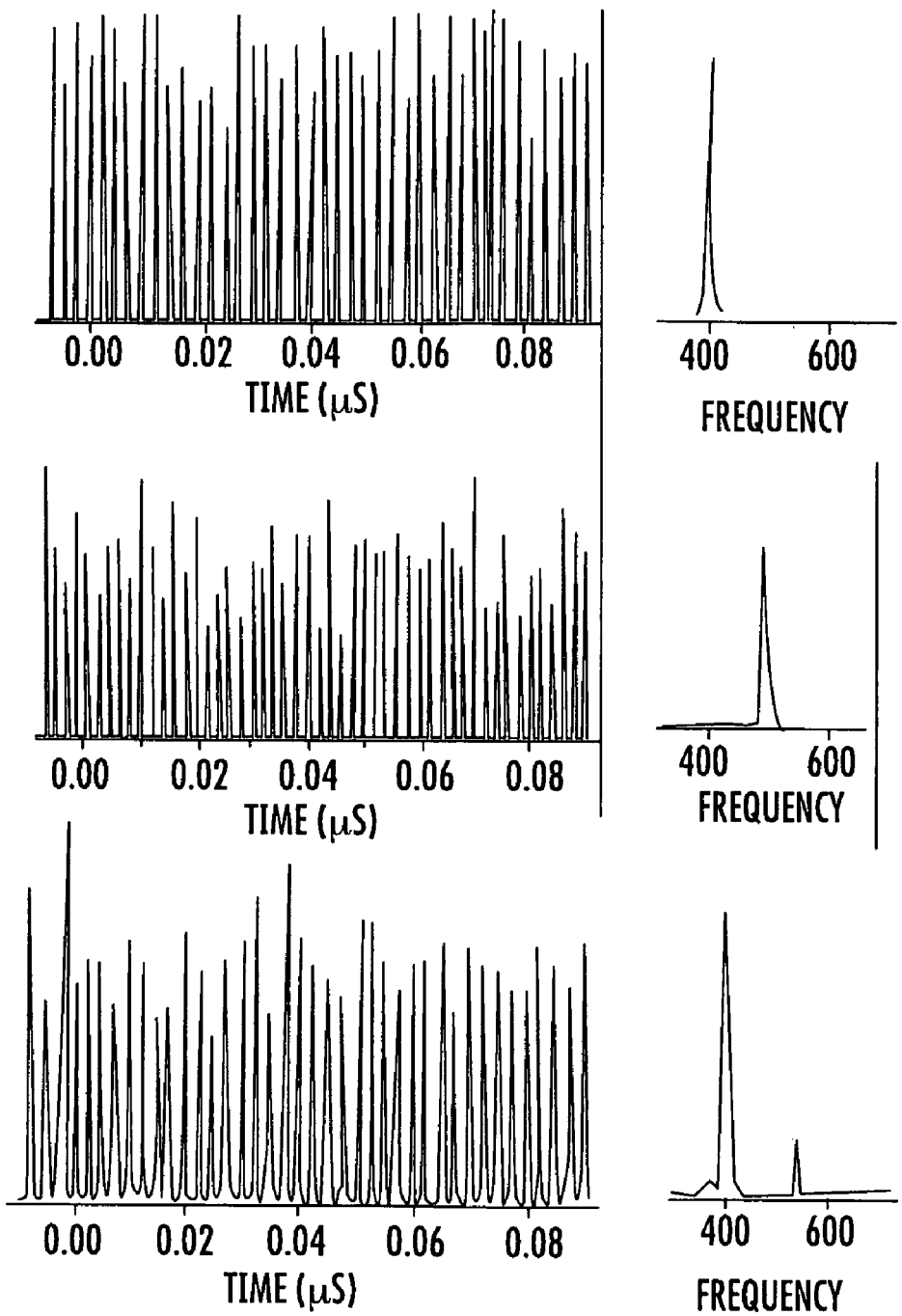
FIGS. 13A-13C are graphs illustrating temporal x-ray signals and corresponding Fourier power spectrum.

FIGS. 13A-13C illustrate graphs of temporal x-ray signals and corresponding Fourier power spectrum. The temporal x-ray signals represent x-ray radiation detected by an Si-PIN photodiode x-ray detector. The graphs on the left of FIGS. 13A-13C represent the temporal x-ray signal. The graphs on the right of FIGS. 13A-13C represent the Fourier power spectrum of the corresponding temporal x-ray signal. The Fourier power spectrum can be generated by applying a temporal digital signal process to the corresponding temporal x-ray signal. The x-ray radiation can be a pulsed x-ray generated by an x-ray source. Referring to FIG. 13A, an x-ray source was pulsed at 400 Hz. Referring to FIG. 13B, an x-ray source was pulsed at 500 Hz. Referring to FIG. 13C, x-ray sources were pulsed at 400 Hz and 500 Hz. The power spectrum graphs demonstrate that the amplitude of an x-ray source at a predetermined frequency can be attributed to originate from the corresponding source.

Figure 14:
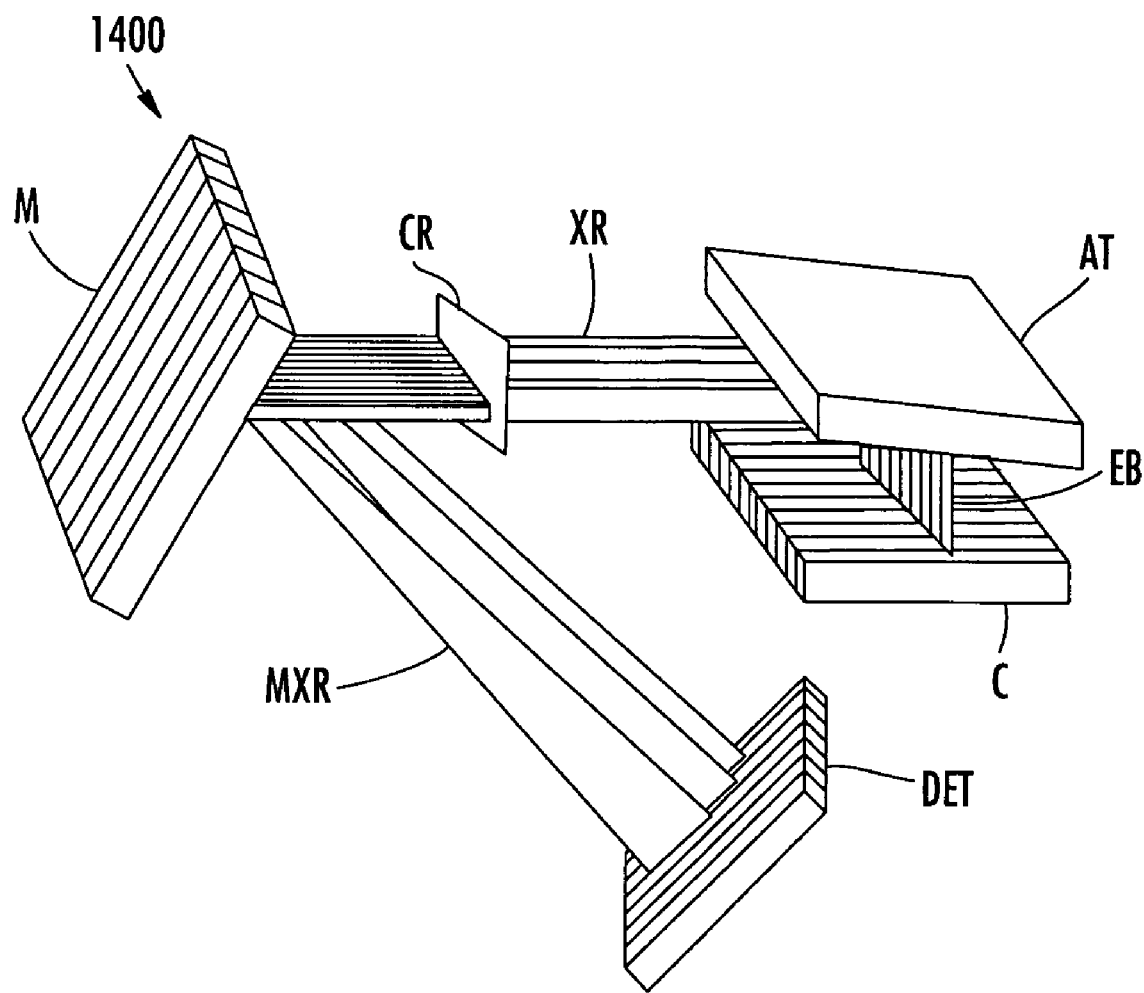
FIG. 14 is a perspective schematic block diagram of a quasi monochromatic micro-CT scanner according to an embodiment of the subject matter described herein.

According to one embodiment, a monochromatic x-rays can be generated and pulsed for obtaining an image of an object to be imaged. FIG. 14 illustrates a perspective schematic block diagram of a quasi monochromatic micro-CT scanner, generally designated 1400, according to an embodiment of the subject matter described herein. Referring to FIG. 14, scanner 1400 can include a cathode C including a plurality of electron field emitters for emitting a plurality of electron beams EB of different frequencies. Electron beams EB can be directed to an anode target AT for generating x-ray radiation XR of different pulsing frequencies. Cathode C and anode target AT can be contained in a pressurized vacuum chamber. X-ray radiation XR can pass out of the vacuum chamber through an electron permeable window made of Be.

X-ray radiation XR can be directed to a collimator CR for collimation. The collimated x-ray radiation XR can be intercepted by a monochromator M for generating monochromatic x-ray radiation MXR. An x-ray detector DET can be positioned for intercepting monochromatic x-ray radiation MXR. An object to be imaged can be positioned between monochromator M and x-ray detector DET for imaging. X-ray detector DET can detect the x-ray radiation and generate temporal x-ray data based on the x-ray radiation. A temporal data analyzer can apply a temporal digital signal process to the temporal x-ray data for removing at least a portion of the temporal x-ray data having different frequencies than the pulsing frequencies of electron beams EB. The resulting temporal x-ray data can be used for generating an image of the object. According to one embodiment, x-ray radiation XR can include a plurality of different x-rays of different pulsing frequencies that are directed at different sides of the object to be imaged.

Figure 15:
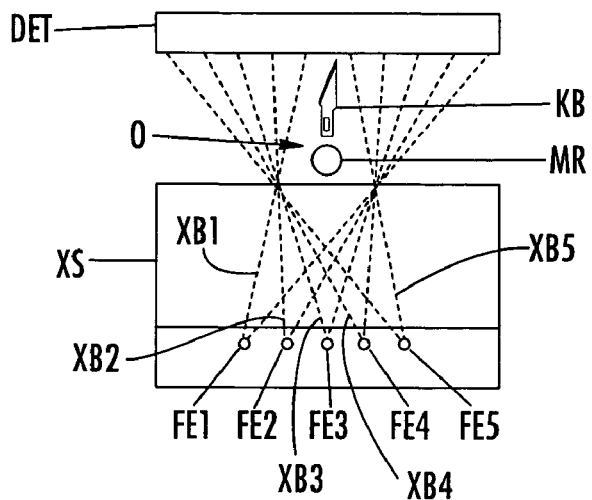
FIG. 15 is a schematic diagram of an arrangement of an x-ray detector and an x-ray source for simultaneous acquisition of multi-projection images of 3-D objects.

As set forth above, an object to be imaged can be positioned for receiving x-ray radiation of different pulsing frequencies from several directions. A 3-D image of the object can be generated by detecting the x-ray radiation from the object while the object is receiving the x-ray radiation of different pulsing frequencies. FIG. 15 illustrates a schematic diagram of an arrangement of an x-ray detector DET and an x-ray source XS for simultaneous acquisition of multi-projection images of 3-D objects O. Referring to FIG. 15, five x-ray beams XB1-XB5 can be generated by electron field emitters FE1-FE5, respectively. X-ray beams XB1-XB5 can be directed at different sides of object O. X-ray source XS and object O can spaced about 15 cm. Object O can include a metal rod MR and a knife blade KB.

The x-ray radiation passing through and around object O can be detected by x-ray detector DET. X-ray detector DET can generate temporal x-ray data based on the detected x-ray radiation. The resulting temporal x-ray data can be used for generating an image of object O according to the subject matter described herein. Referring to FIG. 15, the exemplary object O includes a metal rod positioned in front of a metal knife blade. According to one embodiment, a tomosynthesis image of object O can be obtained that shows a slice of object O that includes knife blade KB and not metal rod MR. According to one embodiment, x-ray detector DET can be a digital 2-D x-ray image sensor having a 1056×1056 pixel array with a 50×50 μm pixel size. X-ray detector DET can be operated at 16 frames-per-second (fps) with 4×4 binning. The imaging conditions can be 40 kVp, 25 μA cathode current, and 5 second exposure time.

Figure 16A:
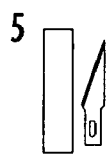
FIGS. 16A-16F are images of an object generated based on x-ray radiation from a plurality of x-ray beams.
Figure 16B:
Figure 16C:
Figure 16D:
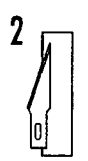
Figure 16E:
Figure 16F:
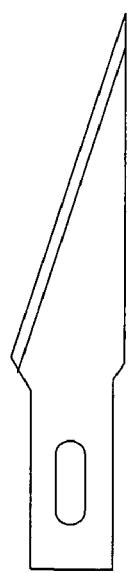

FIGS. 16A-16F are schematic images of object O shown in FIG. 15 generated with x-ray detector DET and x-ray source XS shown in FIG. 15 according to the subject matter described herein. FIGS. 16A-16E are schematic images of object O generated based on x-ray radiation from x-ray beams XB1-XB2, respectively. FIG. 16F is a tomosynthesis image of object O showing a slice of object O that includes knife blade KB and not metal rod MR.

Figure 17:
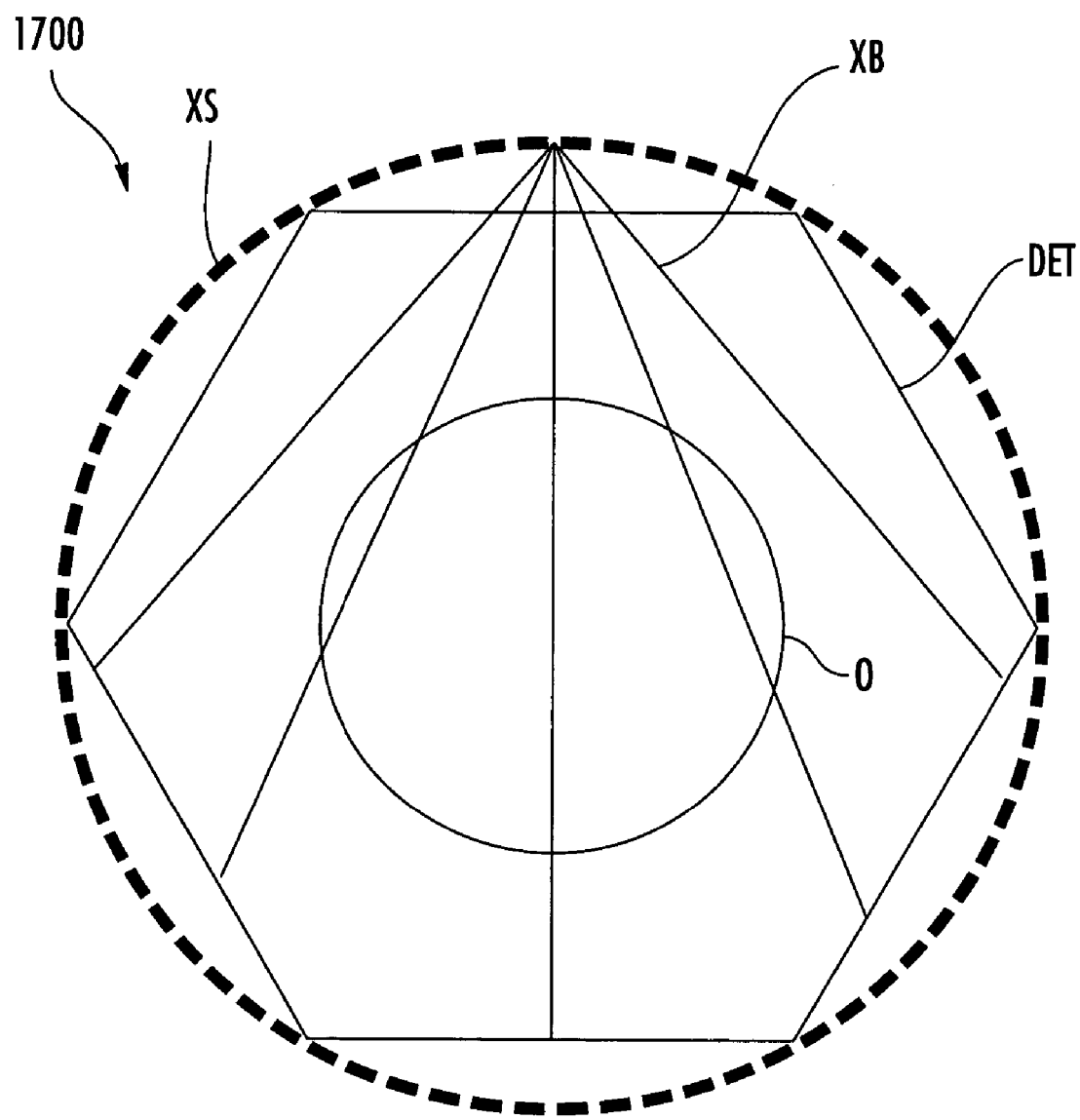
FIG. 17 is a schematic diagram of an exemplary CT imaging system according to an embodiment of the subject matter described herein.

FIG. 17 is a schematic diagram of an exemplary stationary CT imaging system, generally designated 1400, according to an embodiment of the subject matter described herein. Referring to FIG. 17, system 1700 can include a multi-pixel, x-ray source XS in a ring configuration for directing a plurality of x-ray beams towards an object O to be imaged. System 1700 can also include an x-ray detector DET having a plurality of 2-D panels for receiving x-ray radiation. In this example, x-ray detector DET includes six 2-D panels. An x-ray beam XB applied by x-ray source XS can be detected by one or more panels of x-ray detector DET. The x-ray beams can be simultaneously applied to object O.

The plurality of x-ray beams can be pulsed at different frequencies and applied to object O at different angles. X-ray detector DET can detect the resulting x-ray radiation and record the x-ray radiation as temporal x-ray data. A temporal Fourier transform can be applied to the temporal data for simultaneously obtaining multiple projection images. The resulting images can be used to obtain 3-D CT images of object O.

Figures 18A, 18B:
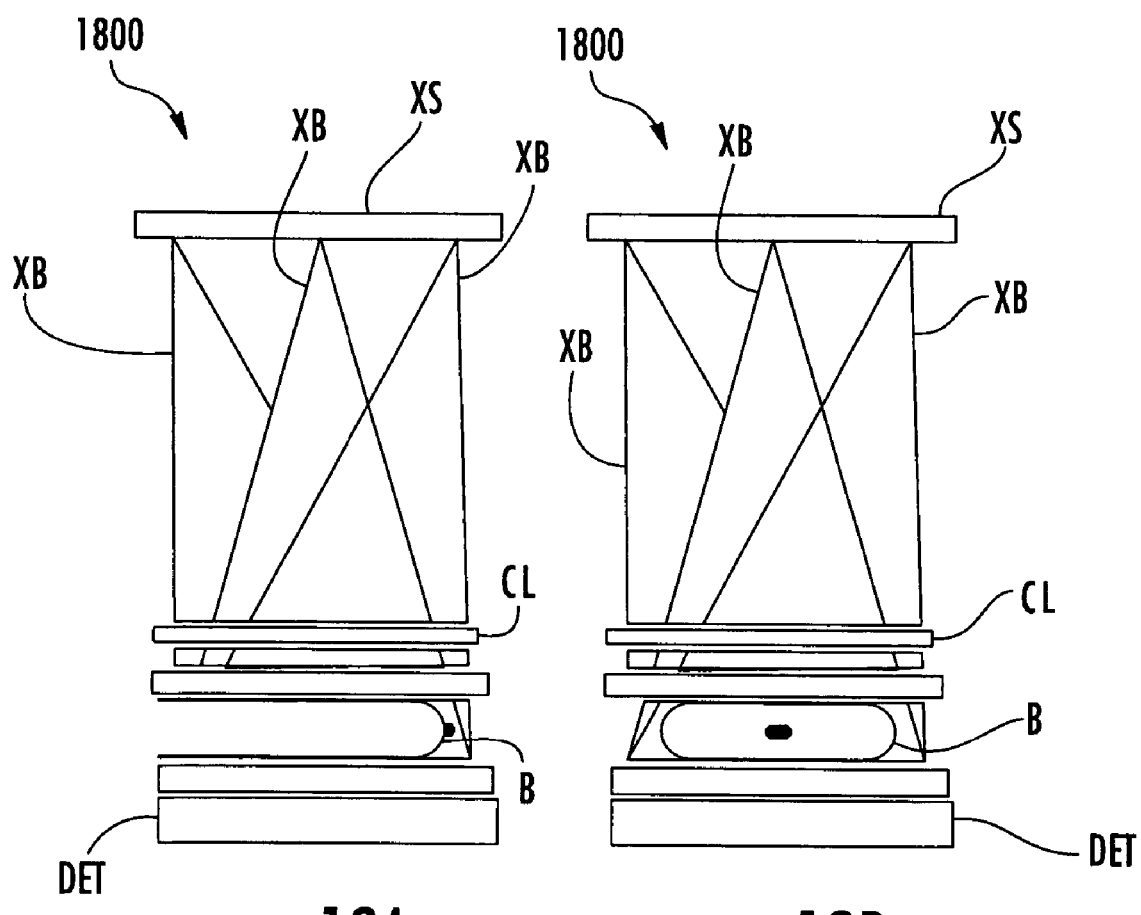
FIGS. 18A and 18B are schematic diagrams of exemplary mammography imaging systems according to embodiments of the subject matter described herein.

FIGS. 18A and 18B are schematic diagrams of exemplary mammography tomosynthesis imaging systems, generally designated 1500, according to embodiments of the subject matter described herein. Referring to FIGS. 18A and 18B, system 1800 can include a multi-pixel, x-ray source XS for generating and directing a plurality of x-ray beams XB towards a breast B to be imaged. System 1800 can also include an x-ray detector DET, such as a photon counting single and multi-line detector. The x-ray beams can be simultaneously applied to breast B. Referring to FIG. 18A, in one embodiment, multi-pixel, x-ray source XS is arranged in such a way that different pixels are distributed along a direction perpendicular to an axis extending from a person's chest to breast nipple. Referring to FIG. 18B, in another embodiment, multi-pixel, x-ray source XS is arranged in such a way that different pixels are distributed along the same direction as an axis extending from a person's chest to breast nipple.

X-ray beams XB can be pulsed at different frequencies and applied to breast B at different angles. Further, x-ray beams XB may be collimated by collimator CL. X-ray detector DET can detect the resulting x-ray radiation and record the x-ray radiation as temporal x-ray data. In accordance with the subject matter described herein, a temporal Fourier transform can be applied to the temporal data for removing at least a portion of the temporal x-ray data having different frequencies than the pulsing frequencies of the x-ray beams. The resulting data can be used to obtain an image of breast B. By simultaneously applying x-ray beams, all projection images of a breast can be obtained in a single scan. A high-quality tomosynthesis image of a breast can be obtained in the same scan span as required for a single mammogram image.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. An x-ray imaging system comprising:
   (a) an x-ray source adapted to generate a pulsed x-ray beam having a predetermined frequency and to apply the pulsed x-ray beam to an object to be imaged;
   (b) an x-ray detector adapted to detect x-ray radiation from the object and generate temporal x-ray data based on the x-ray radiation; and
   (c) a temporal data analyzer adapted to apply a temporal signal process to the temporal data to remove at least a portion of the temporal data having a different frequency than the predetermined frequency.

2. The x-ray imaging system of claim 1 wherein the x-ray source comprises:
   (a) electron field emitters adapted to produce a pulsed electron beam having the predetermined frequency; and
   (b) a target structure positioned to receive the electron beam and generate the pulsed x-ray beam on receiving the electron beam.

3. The x-ray imaging system of claim 2 wherein the electron field emitters comprise components selected from the group consisting of a nanotube, a nanorod, a Spindt tip, and nanoparticles of diamond.

4. The x-ray imaging system of claim 1 wherein the x-ray detector comprises a high-frame rate digital detector.

5. The x-ray imaging system of claim 1 wherein the x-ray detector comprises detectors selected from the group consisting of one or more Si-PIN photodiode x-ray detectors, one or more charge-coupled devices (CCD) area detectors, one or more amorphous selenium (a-Se) area detectors, and one or more amorphous silicon (a-Si) area detectors.

6. The x-ray imaging system of claim 1 wherein the temporal signal process comprises temporal Fourier analysis.

7. The x-ray imaging system of claim 1 wherein the temporal signal process comprises temporal wavelet analysis.

8. The x-ray imaging system of claim 1 wherein the at least a portion of the temporal data having the different frequency corresponds to noise in the detected x-ray radiation.

9. The x-ray imaging system of claim 1 comprising a temporal transform function operable to produce frequency domain power spectrum based on the temporal data.

10. The x-ray imaging system of claim 9 comprising a frequency bandwidth filter operable to filter portions of the frequency domain power spectrum that do not correspond to the predetermined frequency.

11. The x-ray imaging system of claim 10 wherein the frequency bandwidth filter is operable to discard the portions of the frequency domain power spectrum that do not correspond to the predetermined frequency.

12. The x-ray imaging system of claim 1 comprising an object stage operable to rotate the object to different positions with respect to the x-ray beam.

13. A multi-pixel, x-ray imaging system comprising:
   (a) an x-ray source adapted to generate a plurality of pulsed x-ray beams having different predetermined frequencies and to apply the pulsed x-ray beams to an object to be imaged;
   (b) an x-ray detector adapted to detect x-ray radiation from the object and generate temporal data based on the x-ray radiation; and
   (c) a temporal data analyzer adapted to apply a temporal signal process to the temporal data to resolve temporal data having the same frequencies as the predetermined frequencies.

14. The x-ray imaging system of claim 13 wherein the x-ray source comprises:
   (a) electron field emitters adapted to produce a plurality of pulsed electron beams having the different predetermined frequencies; and
   (b) at least one target structure positioned to receive the electron beams and generate the pulsed x-ray beams on receiving the electron beams.

15. The x-ray imaging system of claim 14 wherein the electron field emitters comprise components selected from the group consisting of a nanotube, a nanorod, a Spindt tip, and nanoparticles of diamond.

16. The x-ray imaging system of claim 14 comprising cathodes coupled to the electron field emitters for providing current to the electron field emitters.

17. The x-ray imaging system of claim 13 wherein the x-ray source is operable to wavelet encode the x-ray beams.

18. The x-ray imaging system of claim 17 wherein the temporal data analyzer is operable to wavelet decode the temporal data.

19. The x-ray imaging system of claim 13 wherein the x-ray source includes a plurality of pixels for producing the pulsed x-ray beams, and wherein the x-ray source is operable to apply the pulsed x-ray beams from the different pixels to the object from different angles.

20. The x-ray imaging system of claim 13 wherein the x-ray source is operable to apply the x-ray beams in a predetermined sequence.

21. The x-ray imaging system of claim 13 wherein the x-ray source is operable to apply the x-ray beams simultaneously.

22. The x-ray imaging system of claim 13 wherein the x-ray beams have different x-ray energies.

23. The x-ray imaging system of claim 13 wherein the x-ray detector comprises a high-frame rate digital detector.

24. The x-ray imaging system of claim 13 wherein the x-ray detector comprises detectors selected from the group consisting of one or more Si-PIN photodiode x-ray detectors, one or more charge-coupled devices (CCD) area detectors, one or more amorphous selenium (a-Se) area detectors, and one or more amorphous silicon (a-Si) area detectors.

25. The x-ray imaging system of claim 13 wherein the temporal signal process comprises temporal Fourier analysis.

26. The x-ray imaging system of claim 13 wherein the temporal signal process comprises temporal wavelet analysis.

27. The x-ray imaging system of claim 13 wherein the temporal data having the same frequencies as the predetermined frequencies correspond to the pulsed x-ray beams.

28. The x-ray imaging system of claim 13 comprising a temporal transform function operable to produce frequency domain power spectrum based on the temporal data.

29. The x-ray imaging system of claim 28 comprising a frequency bandwidth filter operable to filter portions of the frequency domain power spectrum that do not correspond to the predetermined frequencies.

30. The x-ray imaging system of claim 29 wherein the frequency bandwidth filter is operable to discard the portions of the frequency domain power spectrum that do not correspond to the predetermined frequencies.

31. The x-ray imaging system of claim 13 comprising a monochromator operable to generate monochromatic, pulsed x-ray beams.

32. The x-ray imaging system of claim 13 comprising a processor operable to simultaneously receive multiple projection images of the object.

33. The x-ray imaging system of claim 32 wherein the processor is operable to reconstruct 3-D images of the object.

34. A method for x-ray imaging, the method comprising:
   (a) applying a pulsed x-ray beam having a predetermined frequency to an object to be imaged;
   (b) detecting x-ray radiation from the object;
   (c) generating temporal data based on the x-ray radiation; and
   (d) applying a temporal signal process to the temporal data to remove at least a portion of the temporal data having a different frequency than the predetermined frequency.

35. The method of claim 34 wherein applying the temporal signal process comprises applying a temporal Fourier analysis.

36. The method of claim 34 wherein applying the temporal signal process comprises applying a temporal wavelet analysis.

37. The method of claim 34 wherein the at least a portion of the temporal data having the different frequency corresponds to noise in the detected x-ray radiation.

38. The method of claim 34 comprising producing a frequency domain power spectrum based on the temporal data.

39. The method of claim 38 comprising filtering portions of the frequency domain power spectrum that do not correspond to the predetermined frequency.

40. The method of claim 39 comprising discarding the portions of the frequency domain power spectrum that do not correspond to the predetermined frequency.

41. The method of claim 34 comprising rotating the object to different positions with respect to the x-ray beam.

42. A method for x-ray imaging, the method comprising:
(a) applying a plurality of pulsed x-ray beams having different predetermined frequencies to an object to be imaged;
(b) detecting x-ray radiation from the object;
(c) generating temporal data based on the x-ray radiation; and
(d) applying a temporal signal process to the temporal data to obtain multiple projection images simultaneously.

43. The method of claim 42 wherein applying the pulsed x-ray beams comprises wavelet encoding the x-ray beams.

44. The method of claim 43 wherein applying a temporal signal process comprises wavelet decoding the temporal data.

45. The method of claim 42 wherein applying the pulsed x-ray beams comprises applying the pulsed x-ray beams to the object from different angles.

46. The method of claim 42 wherein applying the pulsed x-ray beams comprises applying the x-ray beams in a predetermined sequence.

47. The method of claim 42 wherein applying the pulsed x-ray beams comprises applying the x-ray beams simultaneously.

48. The method of claim 42 wherein the x-ray beams have different x-ray energies.

49. The method of claim 42 wherein the x-ray beams are monochromatic.

50. The method of claim 42 wherein applying a temporal signal process comprises applying temporal Fourier analysis.

51. The method of claim 42 wherein applying a temporal signal process comprises applying temporal wavelet analysis.

52. The method of claim 42 wherein applying a temporal signal process comprises producing frequency domain power spectrum based on the temporal data.

53. The method of claim 42 comprising processing the temporal signal to obtain multiple projection images of the object simultaneously.

54. The method of claim 53 comprising processing the temporal signal to obtain 3-D reconstructed CT images of the object using the multiple projection images of the object.

* * * * *